United States Patent [19]

Stamler et al.

[11] Patent Number: 5,612,314

[45] Date of Patent: Mar. 18, 1997

[54] NITROSYLATED NEUROPEPTIDES

[75] Inventors: Jonathan Stamler, Chapel Hill, N.C.; Inigo S. de Tejada, Madrid, Spain

[73] Assignees: Brigham & Women's Hospital; Trustees of Boston University, both of Boston, Mass.

[21] Appl. No.: 426,935

[22] Filed: Apr. 21, 1995

[51] Int. Cl.$^6$ .................................................. A61K 37/00
[52] U.S. Cl. ................... 514/13; 524/14; 524/15; 524/16; 524/17; 530/324; 530/325; 530/326; 530/327; 530/328; 530/329
[58] Field of Search ................ 514/13; 530/324, 530/325, 326, 327, 328, 329; 524/14, 15, 16, 17

[56] References Cited

U.S. PATENT DOCUMENTS 5,380,758  1/1995  Stamler et al. ...................... 514/562
5,439,938  8/1995  Snyder et al. ...................... 514/565
5,508,045  4/1991  Harrison et al. ...................... 424/608

*Primary Examiner*—Edward J. Cain
*Attorney, Agent, or Firm*—Charles J. Herron; Elliot M. Olstein

[57] ABSTRACT

Neuropeptides, particularly vasoactive intestinal peptide(VIP) and fragments, mutations and derivatives thereof that have corresponding activities to which have been directly or indirectly linked at least one NO or $NO_2$ group, and their uses, including the relaxation of smooth muscle in several tissues, including vascular smooth muscle (e.g., aorta) and nonvascular smooth muscle (e.g. trachea, sphincter of Oddi, gastrointestinal smooth muscle and corpus cavernosum smooth muscle), and particularly also for the diagnosis and treatment of human male impotence.

41 Claims, 10 Drawing Sheets

- ● VIP
- ○ VIPGC
- ◆ VIPGC-NO
- ◇ ISOPROTERENOL

-Log dose (M)

VIPGC-NO ($10^{-7}$ M)

VIP ($10^{-7}$ M)

- ● VIP
- ○ VIPGC-NO
- ■ VIPGC
- △ ISOPROTERENOL
- ▲ GS-NO

NITROSYLATED NEUROPEPTIDES

This invention relates to the field of adducts of neuropeptides and fragments, mutations and derivatives thereof, particularly vasoactive intestinal peptide(VIP), that have corresponding activities, and their uses, including the relaxation of smooth muscle in several tissues, including vascular smooth muscle (e.g., aorta) and nonvascular smooth muscle, including trachea, sphincter of Oddi, gastrointestinal smooth muscle, corpus cavernosum smooth muscle and also for the diagnosis and treatment of related disorders including male impotence.

A variety of neuropeptides have been described with potent smooth muscle relaxant activity. These include peptides such as peptide histidine isoleucine (PHIS) and peptide histidine methionine (PHM), substance P, and a series of related naturally occurring peptide derived from mammalian species called tachykinins. These include peptides such as neurokinin A, bradykinin, neurokinin B, and others. The peptide calcitonin gene-related peptide (CGRP) also has smooth muscle relaxant activities in certain tissues, including corpus cavernosum smooth muscle.

VIP is a 28 amino acid polypeptide hormone (Said et al., *Eur. J. Biochem*, 28:199, 1972). It was first isolated in 1969 from normal hog lung and was shown at that time to cause a gradual but prolonged peripheral vasodilation. The polypeptide was given the name vasoactive intestinal peptide (VIP) in 1970 when it was isolated from porcine intestine (Said et al., *Science*, 169:1217, 1970). Since then, it has been isolated and its amino acid sequence determined in rat, pig, cow, guinea pig and human, among other species. The amino acid sequence of VIP isolated from all sources is identical except in guinea pig, where it differs by four non-polar amino acid substitutions. The amino acid sequence of human VIP has been published (Bunnett et al., *Clin. Endocrinol. Metab.* 59:1133–1137, 1984).

VIP immunoreactive neurons and nerve fibers have been found throughout the central nervous system and are widely distributed in many organ systems such as the genitourinary, gastrointestinal, respiratory, and cardiovascular system (Khalil et al., *Vasoactive Intestinal Peptide in Gastrointestinal Endocrinology*, pp 260–272, Ed. J. C. Thompson, McGraw Hill, N.Y., 1987). Gastrointestinal motility is responsible for the orderly movement of secretions and nutrients through discrete anatomic portions of the gastrointestinal tract. An extensive neural and hormonal system regulates this complex mixing and propulsive activity. Neurotransmitters released by gastrointestinal neurons and hormones found in the circulation and enterochromaffin cells are the chemical messengers responsible for coordinating gastrointestinal function.

The action of these messengers on target cells may be contradictory. The circuitry of the enteric nervous system is such that an agent may stimulate a target cell and at the same time stimulate the release of another agent that inhibits the target cell. Thus, the action of an agent on the intact system cannot be predicted by the action on the individual cell. This has been found to be especially true when the data from various in vitro studies using isolated muscle strips exposed to different agents are compared to results seen in a clinical endoscopic setting.

Vasoactive intestinal peptide (VIP) is a potent smooth muscle relaxant in selected tissue beds. In the corpus cavernosum of the penis, relaxation of the trabecular smooth muscle (the erectile tissue) is readily effected by this peptide (Helund et al., *Acta Physiol Scand.* 124:413–419, 1985; Larsen et al., *Invest. Urol.*, 19:211–213, 1981.) The mechanism of action of VIP is classically through increases in intracellular cyclic AMP. Recent data (Ignarro et al., *Biochem. Biophys. Res. Comm.*, 843–850, 1990 and Kim et al., *J. Clin. Invest.*, 88:112–118, 1991) suggest that nitric oxide (NO) mediates the non-adrenergic non-cholinergic relaxation as well as endothelium-dependent-relaxation of corpus cavernosum smooth muscle through increases in tissue cyclic GMP. A major limitation of nitric oxide is its very transient half-life. S-nitrosothiol adducts of nitric oxide have been shown to be useful as delivery mechanisms because they stabilize nitric oxide in bioactive form. VIP and nitric oxide synthase (the enzyme that synthesizes nitric oxide) have been found to co-exist in nerves in the corpus cavernosum (Junemann et al. *J Urol.*, 149:245 A (abstract 127), 1993), indicating they are likely co-neurotransmitters.

The present invention is based on the discovery by the inventors that the combined vascular smooth muscle relaxation actions of nitric oxide and a neuropeptide that has smooth muscle relaxant activity, particularly VIP, and their mediation via multiple pathways, offer the advantages of making relaxation failure less likely than if only one transmitter or mechanism were in place. With this rationale and with the goal of combining the effects of the neuropeptide and NO, a VIP-NO donor has been developed as part of the invention. Because VIP does not have a free thiol susceptible to nitrosylation, a VIP analog (VIP-glycine-crysteine-$NH_2$) was prepared that, in the added cysteine, provides a free thiol functional group. The experiments reported herein show that VIP-G-C maintains the biological activity of VIP and that the free thiol in cysteine can be nitrosylated, making S-nitroso-VIP a NO donor.

The invention provides a compound comprising a neuropeptide or analog, fragment or derivative thereof having vascular or nonvascular smooth muscle relaxant activity to which has been directly or indirectly linked at least one NO or $NO_2$ group, a composition of the compound in a pharmaceutically acceptable carrier or vehicle and uses for the compound and composition.

In one embodiment the neuropeptide is selected from the group consisting of peptide histidine isoleucine, peptide histidine methionine, substance P, calcitonin gene-related peptide and a tachykinin.

In a preferred embodiment the neuropeptide is vasoactive intestinal peptide or analog, fragment or derivative thereof having vascular or non-vascular smooth muscle relaxant activity. A particularly preferred embodiment of this aspect is vasoactive intestinal peptide conjugated with a nitric oxide or nitric oxide-releasing moiety.

As such, the invention relates, inter alia, to vasoactive intestinal peptide(VIP) and fragments, mutations and derivatives thereof that have corresponding activities to which have been directly or indirectly linked at least one NO or $NO_2$ group, and their uses, including the relaxation of smooth muscle in several tissues, including vascular smooth muscle (e.g., aorta) and nonvascular smooth muscle, including trachea, sphincter of Oddi, gastrointestinal smooth muscle, corpus cavernosum smooth muscle and also for the diagnosis and treatment of related disorders including male impotence.

In one aspect the present invention provides vasoactive intestinal peptide and fragments, mutations and derivatives thereof that have corresponding activities to which have been directly or indirectly linked at least one NO or $NO_2$ group. The invention further provides pharmaceutical compositions that comprise a therapeutically effective amount of the vasoactive intestinal peptide or fragment, mutation or derivative thereof that have corresponding activities to which have been directly or indirectly linked at least one NO or $NO_2$ group and a pharmaceutically acceptable carrier or excipient.

In another aspect the invention provides a method for relaxing vascular smooth muscle which comprises contacting said vascular smooth muscle with a vascular smooth muscle relaxing amount of a compound or composition of the invention.

In another aspect the invention provides a method for the treatment of disease states responsive to the prevention or relaxation of undesirable contractions of vascular smooth muscle which comprises administering a vascular smooth muscle relaxing amount of a compound or composition of the invention to an individual in need thereof.

In another aspect the invention provides a method for relaxing non-vascular smooth muscle which comprises contacting said non-vascular smooth muscle with a non-vascular smooth muscle relaxing amount of a compound or composition of the invention.

In another aspect the invention provides a method for the treatment of disease states responsive to the prevention or relaxation of undesirable contractions of non-vascular smooth muscle which comprises administering a non-vascular smooth muscle relaxing amount of a compound or composition of the invention to an individual in need thereof.

In another aspect the invention provides a method for relaxing airway smooth muscle which comprises contacting said airway smooth muscle with an airway smooth muscle relaxing amount of a compound or composition of the invention.

In another aspect the invention provides a method for the treatment of disease states responsive to the prevention or relaxation of undesirable contractions of airway smooth muscle which comprises administering an airway smooth muscle relaxing amount of a compound or composition of the invention to an individual in need thereof.

In another aspect the invention provides a method for preventing or treating an obstructive lung disorder selected from the group consisting of emphysema, asthma, bronchitis, fibrosis, excessive mucous secretion, obstruction of air flow and post-surgical complications which comprises administering to an individual in need thereof an amount effective to prevent or treat an obstructive lung disorder selected from the group consisting of emphysema, asthma, bronchitis, fibrosis, excessive mucous secretion, obstruction of air flow and post-surgical complications of a compound in accordance with the invention in a pharmaceutically acceptable carrier.

In another aspect the invention provides a method for relaxing gastrointestinal smooth muscle which comprises contacting said gastrointestinal smooth muscle with a gastrointestinal smooth muscle relaxing amount of a compound or composition of the invention.

In another aspect the invention provides a method for the treatment of disease states responsive to the prevention or relaxation of undesirable contractions of gastrointestinal smooth muscle which comprises administering a gastrointestinal smooth muscle relaxing amount of a compound or composition of the invention to an individual in need thereof.

In another aspect the invention provides a method for preventing or treating gastrointestinal smooth muscle contractions or spasms associated with an endoscopic procedure which comprises administering to an individual in need thereof an amount effective to prevent or treat gastrointestinal smooth muscle contractions or spasms associated with an endoscopic procedure of a compound in accordance with the invention in a pharmaceutically acceptable carrier.

In another aspect the invention provides a method for relaxing corpus cavernosum smooth muscle which comprises contacting said corpus cavernosum smooth muscle with a corpus cavernosum smooth muscle relaxing amount of a compound or composition of the invention.

In another aspect the invention provides a method for the treatment of disease states responsive to the prevention or relaxation of undesirable contractions of corpus cavernosum smooth muscle which comprises administering a corpus cavernosum smooth muscle relaxing amount of a compound or composition of the invention to an individual in need thereof.

In another aspect the invention provides a method for preventing or treating human male impotence which comprises administering to a human male in need thereof an amount effective to prevent or treat human male impotence of a compound in accordance with the invention in a pharmaceutically acceptable carrier.

The following is a brief description of the drawings which are presented only for the purposes of further illustrating the invention and not for the purposes of limiting the same.

Figure 7A:
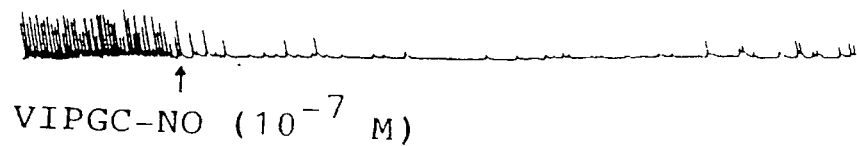

FIGS. 7A and B show a comparison of inhibitions by VIPGC-NO and VIP on spontaneous contraction of rabbit Sphincter of Oddi.

Figure 8:
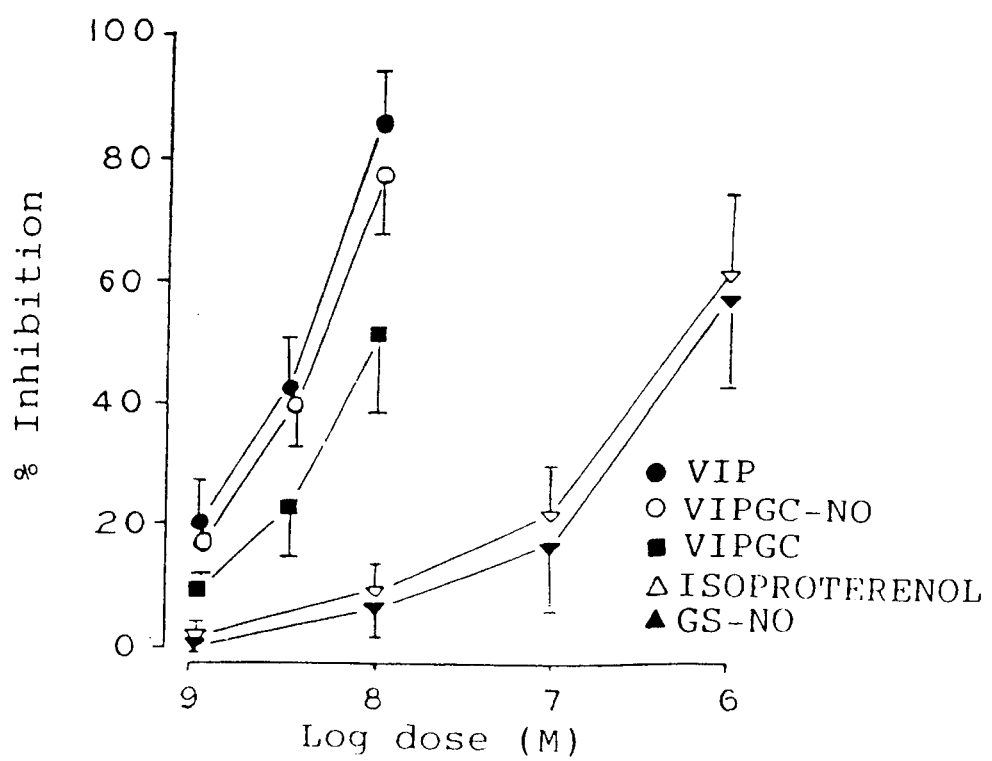

FIG. 8 shows the comparative inhibitory effects of isoproterenol, VIP, VIPGC, VIPGC-NO and GS-NO on contraction amplitude of rat gastric fundus strips.

Figure 9:
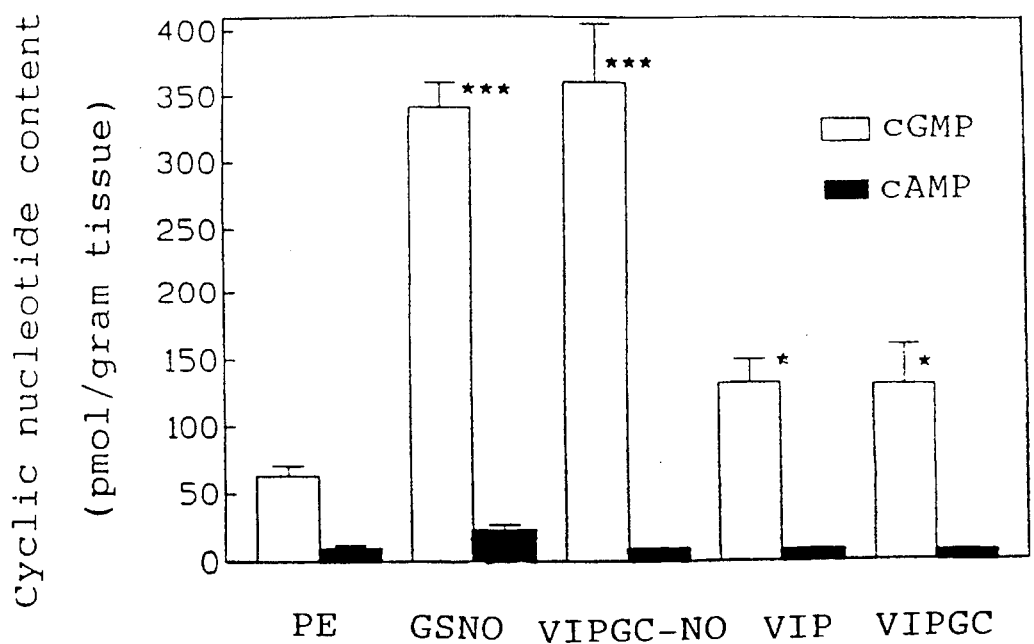

FIG. 9 shows the effects of VIPGC-NO and its analogs on cyclic GMP and cyclic AMP content of rabbit aortic rings.

Figure 10:
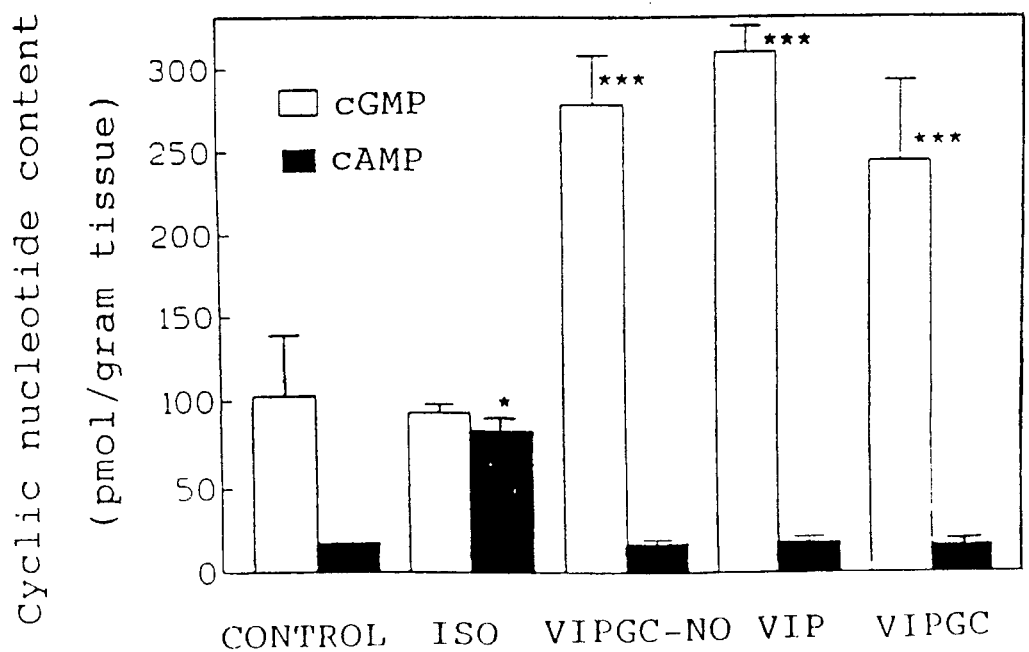

FIG. 10 shows the effects of VIPGC-NO and its analogs on cyclic GMP and cyclic AMP content of guinea pig tracheal ring.

Figure 11:
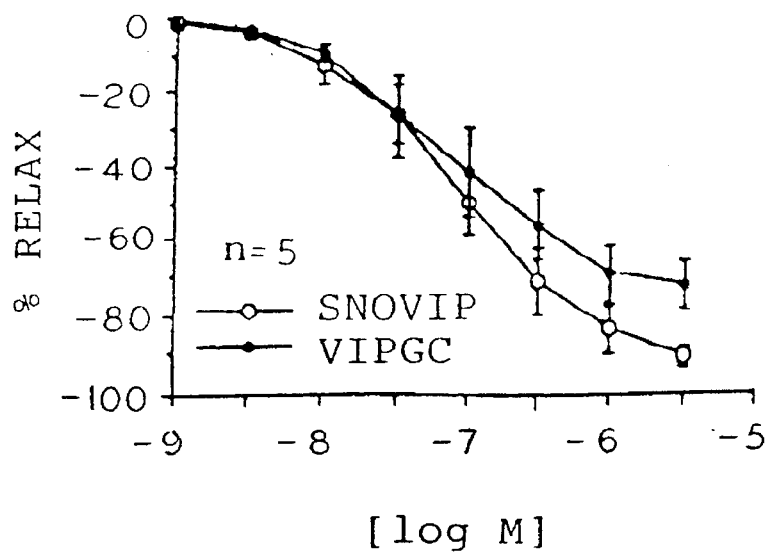

FIG. 11 shows a comparison of the responses of rabbit corpus cavernosum tissue to VIP-Gly-Cys-NO (SNO-VIP) and VIP-Gly-Cys-$NH_2$ (VIP-GC).

Figure 12:
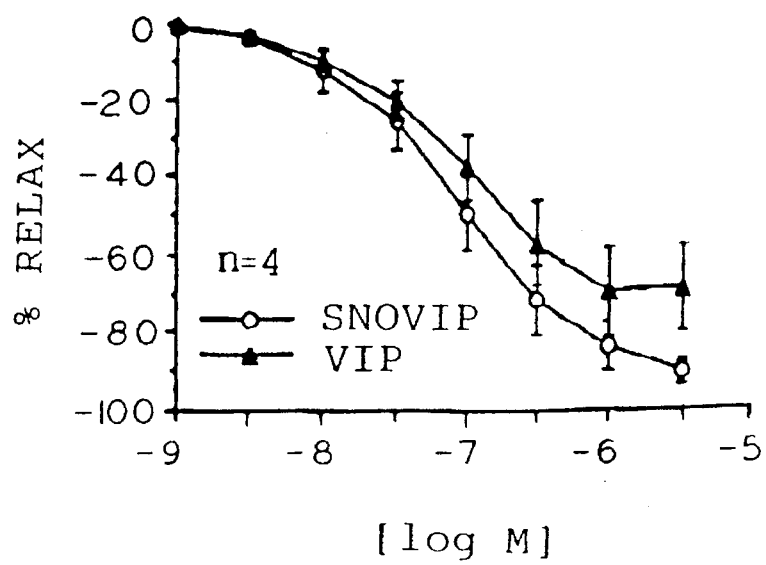

FIG. 12 shows a comparison of the responses of rabbit corpus cavernosum tissue to VIP-Gly-Cys-NO (SNO-VIP) and VIP.

Figure 13:
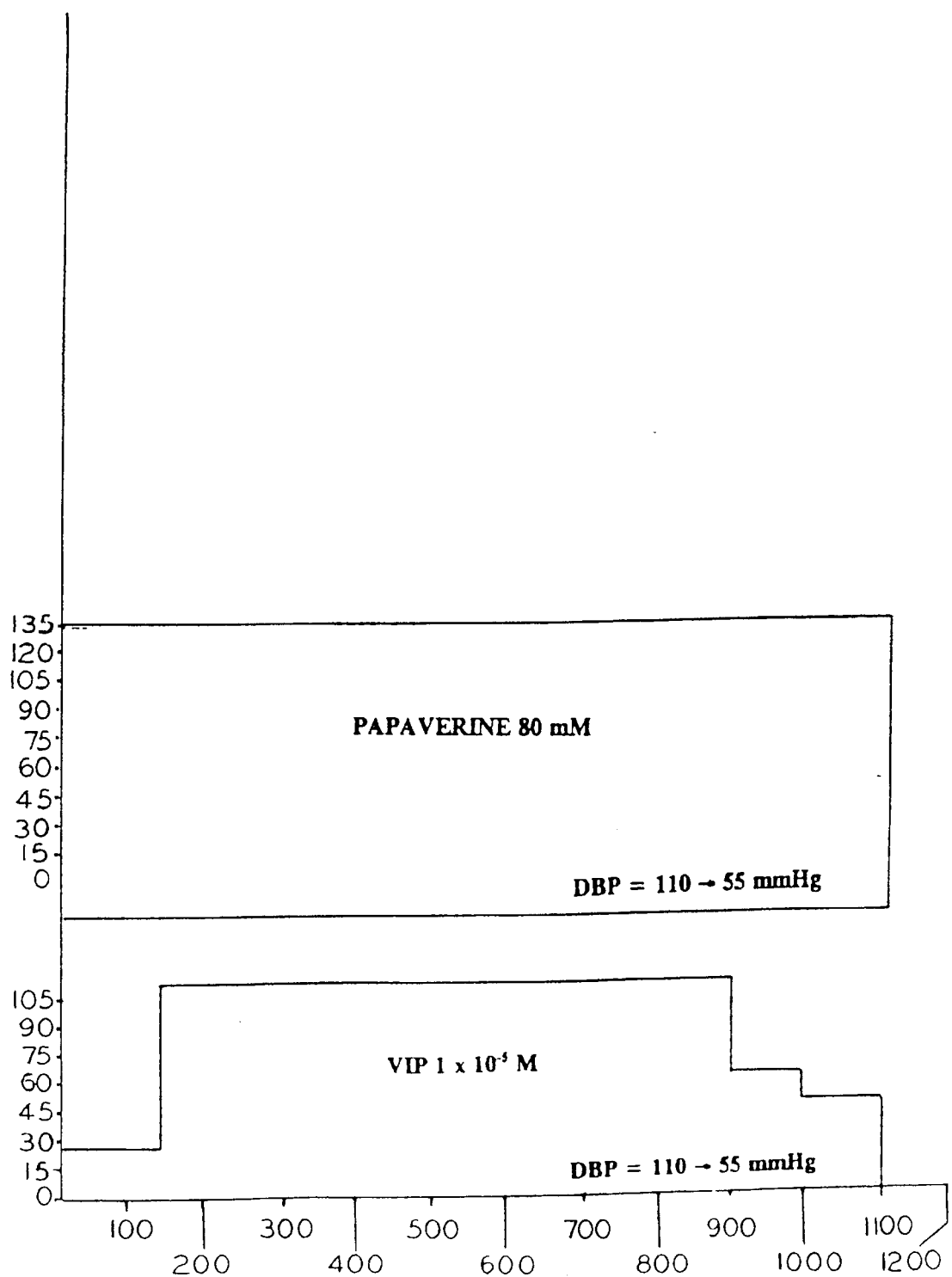

FIG. 13 shows a comparison of the erectile response in vivo in the anesthetized dog following the injection of either VIP or papaverine.

Figure 14:
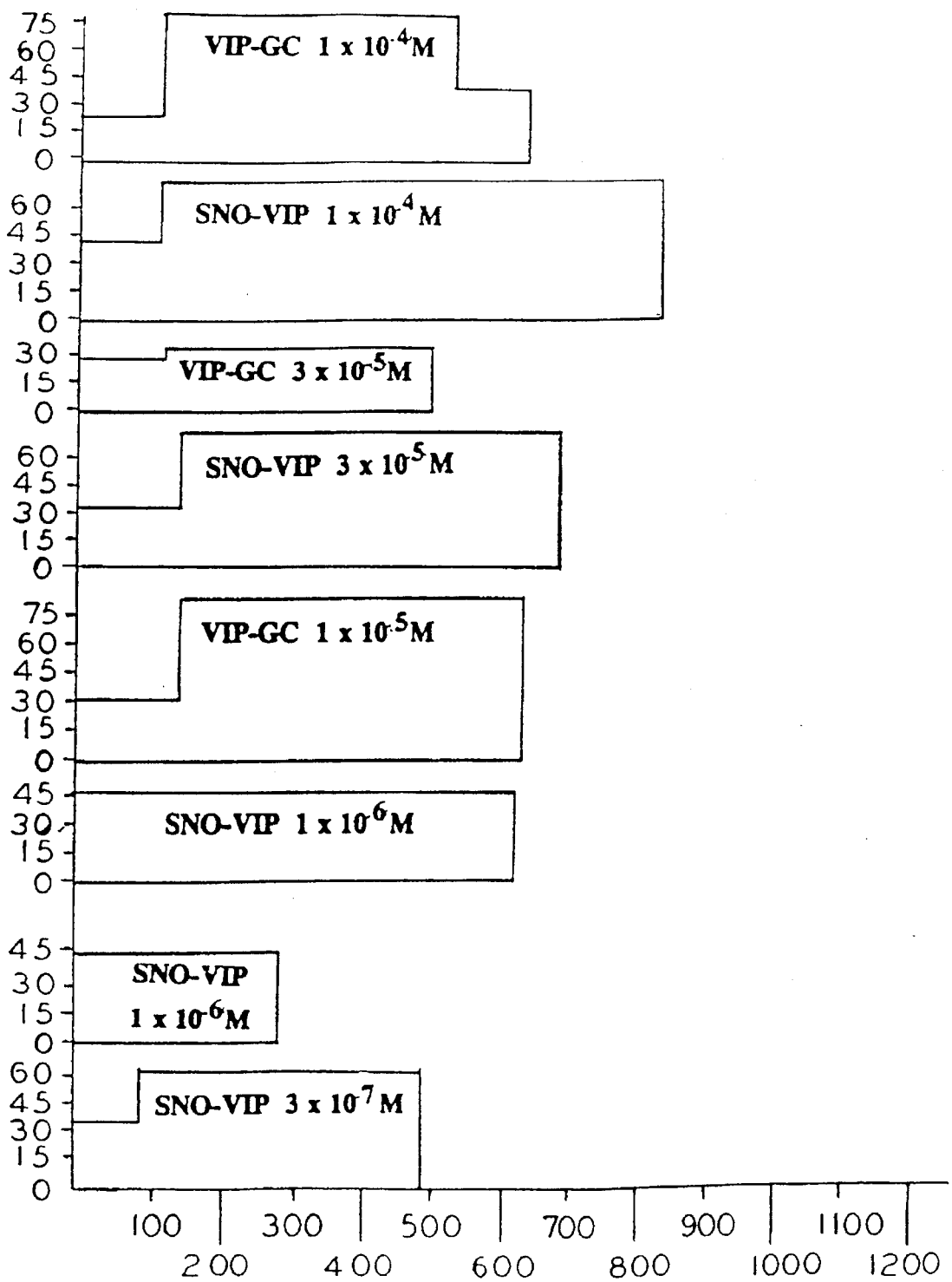

FIG. 14 shows a comparison of the erectile response in vivo in the anesthetized dog upon intracavernosal administration of either VIPGC or SNO-VIP.

Figure 15:
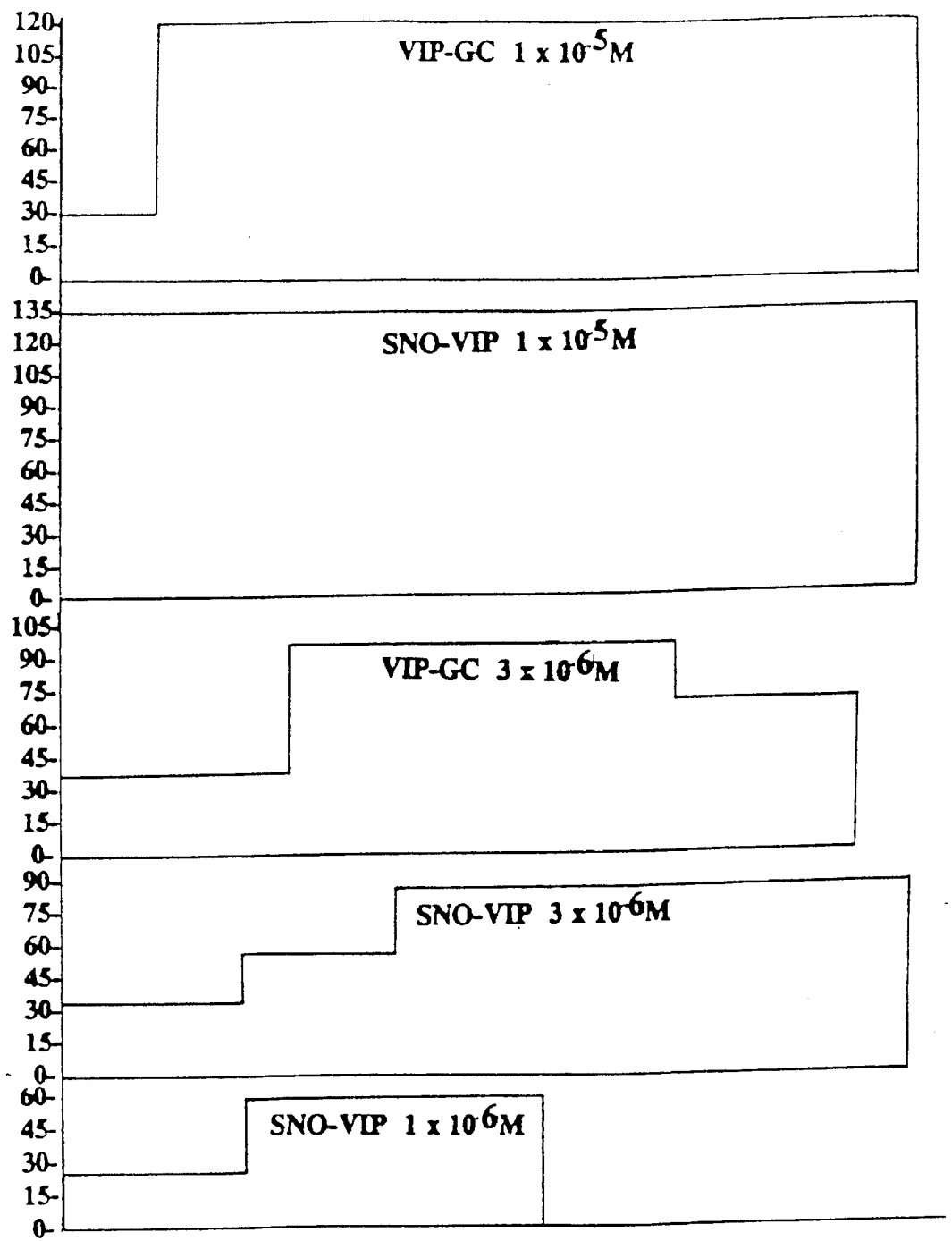

FIG. 15 shows a comparison of the erectile response in vivo in the anesthetized dog upon intracavernosal administration of either VIP-GC or SNO-VIP.

Figure 16:
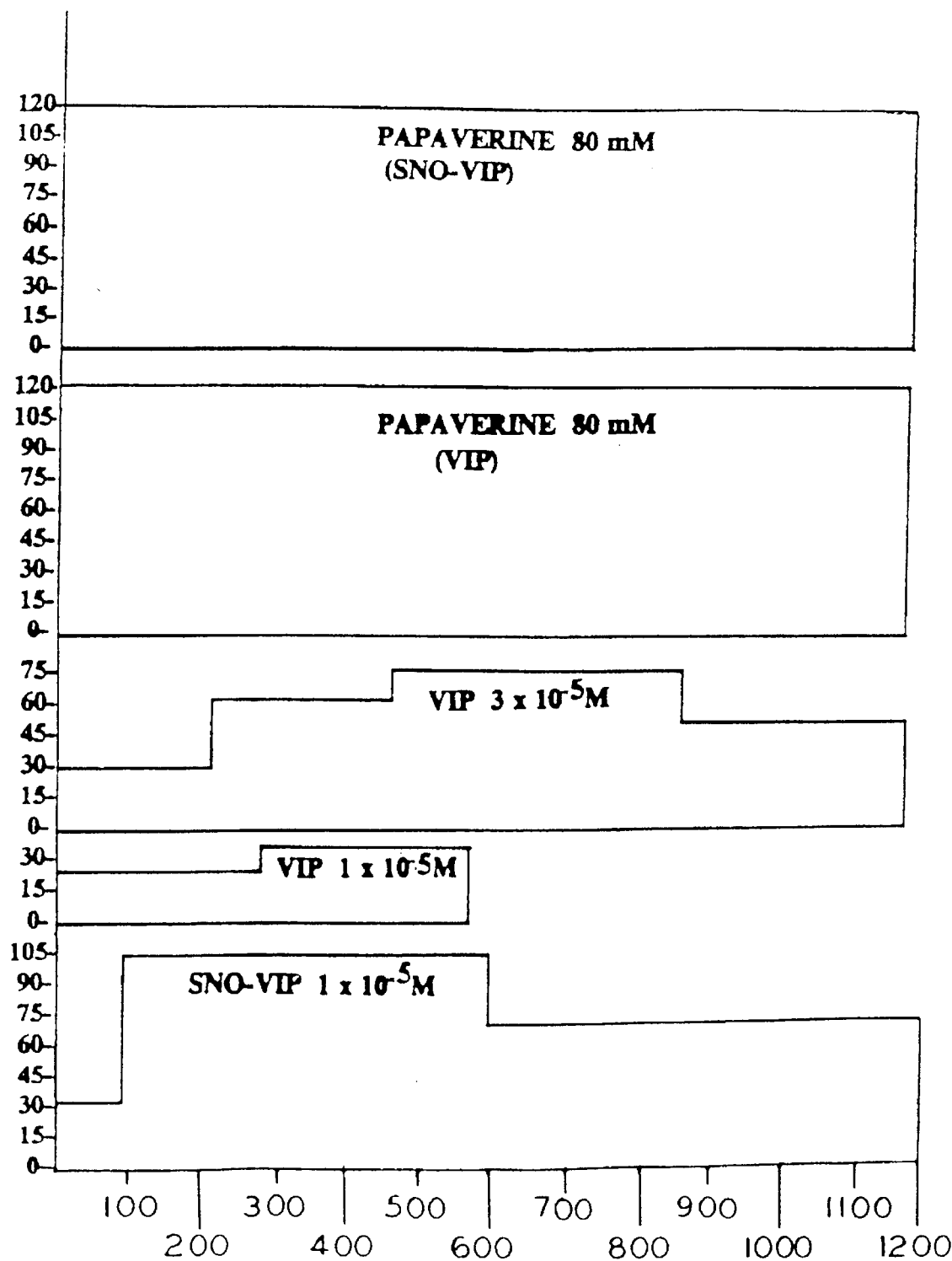

FIG. 16 shows a comparison of the erectile response in vivo in the anesthetized dog upon administration of either VIP, SNO-VIP or papaverine.

As used herein, the term "VIP" refers not only to the carboxyl-amidated protein whose sequence is published in Burnett et al., supra, but also to the functionally active analogs, fragments and derivatives of that protein (particularly amino terminally acetylated derivatives). Not all analogs and derivatives or fragments of VIP species have the same array of pharmacological, therapeutic or diagnostic applications. Thus, the inclusion of analogs, fragments and the like of the disclosed principal embodiment of the VIP analog for the treatment of a particular disorder by effecting smooth muscle relaxation is predicated on the presence of activity particularly related to this disorder.

A VIP analogue or derivative is said to be functionally active when, upon administration to a patient, it is capable of reducing the causative effects resulting in the condition being treated to an extent substantially functionally equivalent to the S-nitrosylated form of the non-nitrosylated polypeptide. Such analogs, fragments and derivatives include VIP species which contain or lack one, two, three, or more amino acids from either the amino or carboxyl terminus. As is known in the art, the amino acids may be present in either their protected or unprotected forms, using appropriate amino or carboxyl protecting groups. The VIP may have a free amine or its amino terminus, or it may be prepared as an acid-addition salt, or acetylated derivative.

Examples of functionally active VIP analogues and functional derivatives, and methods for their preparation are disclosed in U.S. Pat. Nos. 4,605,641; 4,734,400; 4,822,744; 4,835,252; 4,939,224; and 5,055,302, all herein incorporated by reference.

Other applicable analogs specifically include those that include peptide fragments 1–6, 18–28, 15–28, 14–18, and 7–28 of VIP. They have been identified in U.S. Pat. No. 3,862,927.

Other particularly appropriate candidates are those where amino acid 11 is serine rather than threonine, amino acid 13 is phenylalanine rather than leucine, amino acid 26 is valine rather than isoleucine and amino acid 28 is threonine rather than asparagine. These analogs are reported in U.S. Pat. No. 4,237,046.

Also applicable are amino acid residue fragments from amino acids 11–23 of VIP, particularly including at least residues 15–20 and the known analogs thereof. These are reported in U.S. Pat. No. 4,737,487.

Other candidates for activity are VIP species having amino acids that are protected by carboxyl or carboxyalkyl or aryl groups optionally substituted with halonitro lower alkyl or lower alkyoxy moieties including cycloalkyls and aralkyl moieties. These can be complex alkyl moieties including alkaryl, vinyl, isonicotinyl or adamantyl or phthaloyl, tosyl or formyl moieties. Various blockers or extenders in the form of alkyl moieties or various amino acid extension fragments can be added to the carboxyl and amino termini of the VIP sequence and are also contemplated as suitable for application to the treatment of erectile dysfunction upon confirmation of activity.

In general, synthesis of polynitrosated peptides and proteins can be achieved in several ways. 1) Mono S-nitrosylation is best achieved by incubating peptides and proteins (in deionized water in an equimolar concentration of acidified nitrite (final concentration 0.5N HCL) for a period of 1–30 minutes. The incubation time depends on the efficiency of nitrosation and the tolerance of the protein. Nitrosation can also be achieved with a variety of other mitrosating agents including compounds such as S-nitrosocysteines, S-nitrosoglutathione and related alkyl nitrites. These compounds are to be used when the peptide or protein does not tolerate harsh acidic conditions.

There are two ways of achieving poly S-nitrosation. In the first, the peptide or protein is reduced in 100–1000 molar excess dithiothreitol for 30–60 minutes. This exposes intramolecular thiols. The peptide or protein is separated from dithiothreitol by gel filtration (G-25). The protein is then exposed to increasing concentrations of acidified nitrite (0.5N HCl) in relative excess over protein. Complementary measurements of Saville indicate when S-nitrosation is complete. For example, with albumin, this procedure leads to approximately 20 intramolecular S-NO derivatives.

Alternatively, the protein can be treated with thiolating agent such as homocysteine thiolactone. This tends to add homocystine groups to exposed amine residues in proteins. The derivatized protein can then be S-nitrosated by exposure to acidified nitrite. Exposure to increasing concentrations of nitrite with complementary measurements of Saville can be used to ascertain when S-nitrosation is maximal. Alternatively, thiol groups can be quantified on the protein using standard methodologies and then the protein treated with a stoichiometric concentration of acidified nitrite (0.5N HCl).

Polynitrosation of nucleophilic functional groups (other than thiol) can be achieved when proteins are incubated with excess acidified nitrite. The order of protein reactivity is tyrosine followed by amines on residues such as trytophan. Amide linkages are probably less reactive. Accordingly, many NO groups can be added to proteins by simply incubating the protein with high excess acidified nitrite. For example, exposure of albumin to 1000 fold excess nitrite leads to approximately 200 moles of NO/mole protein. These experiements are performed in 0.5 normal HCl with incubations for approximately one hour. $^{15}$N NMR can be used to determine where the addition (or substitution) by NO takes place.

Further, nitrosation can be achieved by exposure to authentic nitric oxide gas under anaerobic conditions. For successful nitrosation proteins should be incubated in at least 5 atmospheres of NO gas for several hours. Incubation time is protein specific. This can lead to NO attachment to a variety of protein bases. Best characterized reactions involve primary amines. This mechanism provides a pathway to sustain N-nitrosation reactions without deamination. Specifically, exposure to acidified nitrite would otherwise lead to deamination of primary amines whereas this method leads to formation of N-hydroxynitrosamines with potent bioactivity. Similar substitutions at other basic centers also occur.

Further background on techniques for nitrosylation of amino acids and polypeptides can be obtained from PCT Published Application No. WO 93/09806 the entirety of which is incorporated by reference herein.

Having been made aware of the presently disclosed nitrososylated "VIP" analogs and the numerous other exemplary compounds specifically disclosed herein, routine screening methods will provide other of the analogs, fragments and the like which have activity specifically related to the relaxation of various types of smooth muscle in accordance with this invention.

Although the invention is not bound by any theory or particular mechanism of action, the inventors have arrived upon a new concept of combining cyclic GMP dependent knase activity and cyclic AMP dependent kinase activity (vasodilation) in a single class of novel compounds, the nitrosylated analogs and active fragments and derivatives of VIP. Thus, advantage has been made of two mechanisms of smooth muscle relaxation, including vascular and non-vascular smooth muscle in a single therapeutic compound. These compounds and their uses are principal aspects of the present invention.

The term "impotence" refers to a condition of male sexual dysfunction which is characterized by the inability to obtain or maintain an erection. Smooth muscle has a critical role in erectile function. The nitric oxide adducts of VIP analogs relax corpus cavernosum smooth muscle.

The term "corpus cavernosum" refers to two adjacent cylindrical structures that communicate in the distal two-thirds of the penis, and together with the corpus spongeosum that surrounds the urethra, constitute erectile tissue. This erectile tissue consists of an irregular sponge-like system of vascular spaces interspersed between arteries and veins. Erection occurs when cavernosa smooth muscle relaxation causes a decrease in arterial resistance and resulting increase in arterial blood flow to the penis. The penile arteries dilate, increasing blood flow and pressure in the corpora, and traebecular smooth muscle relaxes, trapping blood within the corpus cavernosum.

Organic causes of erectile impotence may include endocrine, drug-induced, local injury, neurologic, and vascular. In particular, impotence may result from neurologic blockade caused by such drugs as antihistamines, antihypertensives, psychogenic agents, and anticholinergics. Impotence may also result from neurologic disorders such as interior temporal lobe lesions, spinal cord disorders, and insufficiency of sensory input resulting from diabetic neuropathy. Pelvic surgery, generally for cancer, can disrupt the pelvic plexus that innervates the penis. An additional, and probably most common, cause of impotence is insufficient blood flow into the vascular network resulting from an intrinsic defect, or from penile trauma.

Currently available methods for treating impotence consist largely of surgical techniques and intracavernosal injections of pharmacological agents. One surgical technique involves the implantation of a penile prosthesis by inserting within the corpora, a small silicone rod. However, the penis remains in a constant state of erection. Alternatively, an inflatable prosthetic device may be implanted on each corpus, with a connecting reservoir of material placed in the retroperitoneal space. Erection is achieved through the use of pumps which are located in the scrotum. The complication rate is higher than with the silicone rod.

Intracavernosal injection of the smooth muscle relaxant, papaverine has been used to induce erections. However, a significant disadvantage of this treatment method is that numerous side effects and complications result from the chronic use of drugs such as papaverine. High frequency of fibrosis (papaverine), priapism and pain ($PGE_1$) have been observed with the use of drugs such as papaverine and $PGE_1$. There is also a high failure rate with such drugs and so a need exists for alternate drug therapies.

The compounds of the invention offer several unique advantages. They stabilize nitric oxide in a bioactive form for delivery. They provide a unique compound with a unique mechanism of action including a cyclic AMP relaxation response, and a cyclic GMP-dependent relaxation response. And, they are small and therefore readily amenable to delivery by injection into the corpus cavernosum, by intraurethral or topical administration. Having the biological activity of the putative endogenous modulators of penile erection, VIP and NO, and a treatment for erectile dysfunction using the compounds. These compounds are believed to have a unique mechanism of action resulting in increases in both cyclic AMP and cyclic GMP and therefore offers a unique therapeutic approach to treatment of erectile dysfunction.

The effect of nitrosylation on VIP and its various analogs can be tested in vitro in organ chambers. Rabbit corpus or human corpus cavernosum tissue is suspended in organ chambers to determine isometric tension. Tissues are contracted with an alpha adrenoceptor agonists (norepinephrine, phenylephrine) and once a stable contraction is reached, the relaxant effects of the various VIP/VIP analogs (nitrosylated or not) are compared by the cumulative addition of each molecule to an organ chamber. Multiple chambers are set simultaneously (8 to 16), which allows the comparison of bioactivity of multiple analogs under the same conditions. This technique allows the determination of the Threshold concentration, and EC50 and the EC max for relaxation of corpus cavernoum smooth muscle for each molecule.

Other procedures for screening analogs involve the use of a cell line that has receptors for VIP and that responds to the exposure of VIP or its analogs through the release of substance that can be measured (e.g., cell line that release GH and/or prolactin in response to VIP). This procedure allows simultaneous screening of multiple analogs, e.g. 10–40.

The invention also relates to pharmaceutical compositions containing the compounds of the invention together with a pharmaceutically acceptable carrier.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

In a preferred embodiment, the composition is formulated in accordance with routine procedures as a pharmaceutical composition adapted for administration to human beings by injection into the corpus cavernosum or by intraurethral or topical administration.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1, 3-butanediol. Among the acceptable vehicles and solvents that may be employed are water, Ringer's solution, and isotonic sodium chloride solution. In addition, sterile, fixed oils are conventionally employed an a solvent or suspending medium. For this purpose any bland fixed oil may be employed including synthetic mono- or diglycerides. in addition, fatty acids such as oleic acid find use in the preparation of injectables.

Typically, compositions for injectible administration are solutions, suspensions or emulsions in sterile isotonic aqueous buffer. Suitable injection vehicles include but are not limited to saline, buffered saline, dextrose, water, glycerol, and combinations thereof. The formulation should suit the mode of administration. The composition, if desired, can also contain minor amounts of wetting or emulsifying agents, or pH buffering agents. Where necessary, the composition may also include a solubilizing agent and a local anesthetic to ameliorate any pain at the site of the injection.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic composition of the invention which will be effective in the treatment of a particular disorder or condition will depend on the degree of apparent severity or extent of the disorder. Suitable dosage ranges for intracavernosal administration are generally about 1 to 3 μg of VIP in a bolus injection. Effective doses may be extrapolated from dose-response curves derived from in vitro or animal model test systems.

While the compounds of the invention can be administered as the sole active pharmaceutical agent, they can also be used in combination with one or more compounds which are known to be effective against the specific disease state that one is targeting for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

EXAMPLE 1

Synthesis of VIP-Gly-Cys-NO from VIP-Gly-Cys(Acm)-NH$_2$

This example reports synthesis of an S-nitrosopeptide VIP analog where the native peptide is provided with a cysteine residue.

VIP and the VIP family of peptides have no free cysteine residues. In light of this, modifications must be made for it to be S-nitrosylated. An S-nitrosylated derivative can be synthesized by two methods that require addition of thiol. This can be accomplished by: a) thiolation of the natural peptide; and b) synthesis of a novel peptide with an additional cysteine residue. The latter method offers an advantage in that it provides the opportunity of adding combinations of amino acids that can be tested for improved potency. The novel peptide product bearing thiol is then S-nitrosylated, for example, as follows.

VIP-Gly-Cys-NH$_2$ peptide

VIP-Gly-Cys-NH$_2$ (MW 3486) was synthesized by solid state peptide synthesis methods employing amino acids whose α-amino moieties were protected with an Fmoc (9-fluorenylmethoxycarbonyl) group. Successive amino acids were coupled to the nascent peptide by activation with 2-(1H-benzotriazol-1-yl)-1,1,3,3,-tetramethyluronium hexafluorophosphate (HBTU). Amino acid side chains were protected as follows:

His-Ser(tBu)Asp(OtBu)-Ala-Val-Phe-Thr(tBu)-Asp(OtBu)-Asn (Trt)-Tyr(tBu)-Thr(tBu)-Arg(Pmc)-Leu-Arg(Pmc)-Lys (Boc)-Gln(Trt)-Met-Ala-Val-Lys(Boc)-Lys(Boc)-Tyr(tBu)-Leu-Asn (Trt)-Ser(tBu)-Ile-Leu-Asn(Trt)-Gly-Cys(Trt)-[NH]

where tBu=tert-butyl, OtBu=tert-butyl ester, Trt=Trityl, Pmc=2,2,5,7,8-pentamethylchroman-6-sulfonyl and Boc=tert-butyloxycarbonyl.

The completed peptide was cleaved from the solid support and deprotected by treatment with 95% trifluroacetic acid, phenol, ethandithiol and thioanisole followed by precipitation in ice cold diethyl ether. It was redissolved in 1% acetic acid, purified by reversed phase-HPLC and lyophilized from 0.1% trifluoroacetic acid. The amino acid composition and peptide content were determined by amino acid analysis.

The peptide was S-nitrosated as follows. Lyophilized peptide was dissolved in 1M HCl . Thiol content was determined using Ellman's reagent. An equivalent of NaNO$_2$ was added to the peptide solution and allowed to react for 5 minutes at room temperature. Formation of S-NO was determined by the Saville assay in which NO displaced from thiol groups by $Hg^{2+}$ is assayed by diazotization of sulfanilimide followed by coupling with the chromophore N-(1-naphthyl)-ethylenediamine (Saville, Analyst (London), 83:670–672 (1958)). The pH of the peptide solution was adjusted to about 3 with NaOH and the SNO-peptide was passed through a reversed phase HPLC column and lyophilized.

EXAMPLE 2

In Vitro Tissue Relaxation Using Nitrosylated VIP Analog

Preparations of rabbit aortic rings and tension recording

The preparation of rabbit aortic rings was similar to that described previously (Jia and Furchgott, 1993). Briefly, male New Zealand rabbits weighing 1.5 to 2.0 Kg were anesthetized by an intravenous injection of sodium pentobarbital (40 mg/kg) into a marginal ear vein. The descending thoracic aorta was quickly removed and placed in ice-cold Krebs' solution containing the following composition (mM): NaCl, 118; KCl, 4.8; MgSO$_4$, 1.2; CaCl$_2$, 2.5; KH$_2$PO$_4$, 1.2; NaHCO$_3$, 25; glucose, 11; Na$_2$EDTA, 0.03. The thoracic aorta was first trimmed free of most adipose and connective tissue. It was then cut into transverse rings by placing it at a right angle across five parallel razor blades mounted at 2.5 mm intervals in a plastic holder and then rolling a large polypropylene pipette tip over it (simultaneously producing four rings of equal size). The aortic rings and other tissues (see the following) used in this study, were mounted on pairs of L-shaped hooks and suspended in Krebs' solution (gassed with 95% O$_2$/5% CO$_2$, 37° C.) in 20 ml organ chambers unless stated otherwise.

Tension was measured isometrically using Grass FT03C transducers, and was displayed on model 7 Grass polygraphs (Grass Instruments, Quincy, Mass. Rings and other tissues used (see the following) in this study were allowed to equilibrate for at least 90 minutes with four times rinse before experiments were begun unless stated otherwise. Basal tension was maintained at approximately 2 g. Most experiments were carried out on sets of four rings from the same aorta. To allow studies on relaxation, each ring was precontracted submaximally (30–70% of maximum tone) by addition of 200 nM PE to the bathing solution. Results are expressed in percentage of relaxation of phenylephrine-induced tone.

Preparation of airways

Male Hartley guinea pigs (300–400 g) were anesthetized by use of intraperitoneal injection of pentobarbital sodium (40 mg/kg) to achieve a deep plane of anesthesia. The tracheas were dissected out, transferred to cold Krebs' solution. Tracheas were then dissected free from surrounding fat and connective tissue and cut transversely between the segments of cartilage, so as to give tracheal rings about 2 mm thick. The rings were suspended between stainless-steel hooks in the 20 ml organ baths containing the above-mentioned Krebs' solution at 37° C. The hooks were connected to the FT03C transducers. Rings were equilibrated at a basal tension of 1 g as described above and then primed twice with methacholine (100 nM). The rings were rinsed throughout after each priming exposure. Tracheal rings were not used if they could not sustain at least 1 g tension when exposed to 100 nM methacholine. The surface of organ baths was treated with 1N HCl to minimize contamination and allowed to dry in room air before Krebs' solution were added. For relaxation studies, methacholine (100 nM) was used to contract the tracheal rings and results are expressed in percentage of relaxation of methacholine-induced tone.

Preparation of rabbit sphincter of Oddi

The preparation of rabbit sphincters of Oddi (SO) was similar to that described previously (Slivka et al. 1994) with minor modifications. Briefly, the rabbit abdomen was opened at the midline. The gall bladder, bile duct, gastric antrum and contiguous duodenum were isolated, removed en bloc, and transferred to ice cold Krebs' solution at pH 7.4. The duodenum was opened along the antimesenteric border as was the adjacent pylorus and gastric antrum. From the luminal surface, the ampulla of Vater was identified and the SO isolated on ice under an illuminated magnifier by sharp dissection.

The SO were mounted on pairs of the hooks and suspended in organ chambers containing the Krebs' solution at 37° C. Resting tension was adjusted to 1 g, and circular contractions were monitored by the FT03C force transducer and recorded on the model 7 Grass polygraphs. SO were allowed to equilibrate as described above. To investigate the direct effects of VIP and its S-nitrosylated analog VIPGC-NO on SO contraction frequency and amplitude, varying concentrations of the two compounds as well as VIPGC and GSNO were added to organ baths. Some experiments were performed by using ACh to intensify SO contractility, and then the effects of VIP, VIPGC-NO, VIPGC and GSNO on SO contractility were tested. After each experimental observation was complete, the SO were washed at least three times with fresh Krebs' solution.

Preparation of rat gastric fundus

Male and female Sprague-Dawley rats weighing 200–300 g were anesthetized with 40 mg/kg sodium pentobarbital given intraperitoneally. After deep anesthesia was obtained, exsanguination was accomplished by severing both the jugular vein and common carotid artery. The abdomen was opened at the midline and the stomach was removed, and transferred to the ice cold oxygenated Krebs' solution at pH 7.4. The stomach was dissected out and the pink pyloric end cut away from the grey fundal end. The fundal end was split open so as to form a sheet, the contents were washed away. Longitudinal muscle strips (3×20 mm) of the gastric fundus were prepared as described by Vane (Vane, Br. J. Pharmac. Chemother., 12:344, 1957). The strips were mounted under a 1-g resting tension between two parallel platinum electrodes placed inside the organ baths containing 20-ml of the gassed Krebs' solution. The Krebs' solution also contained atropine (1 µM) and guanethidine (4 µM) to block cholinergic and adrenergic involvement in response to field stimulation of intramural nerves and 5-hydroxytryptamine (5-HT, 5–10 µM) to raise the tone of the smooth muscle. In some experiments, indomethacin (10 µM) was present in Krebs' to avoid the influence of endogenous prostaglandins. Tissues were allowed to equilibrate for 1 h with changes of Krebs' solution every 10 minutes.

After the equilibration period, relaxations of smooth muscle were elicited by VIP, VIPGC, VIPGC-NO, isoproterenol and GSNO. In some experiments, the strips were incubated for 10 minutes with $N^G$-monomethyl L-arginine (L-NMMA).

Measurement of cyclic nucleotide

In order to assess the mechanism of relaxation induced by VIPGC-NO and its analogs, tissues exposed to these compounds to the period of the peak relaxation (10 minutes required for vessel relaxation, 5 minutes and 20 minutes required for tracheal relaxation induced by Iso and VIPGC-NO and its analogs, respectively) were immediately frozen in liquid nitrogen. Frozen tissues were homogenized in ice-cold 6% trichloroacetic acid to give approximately a 10% (w/v) homogenate. The homogenates were centrifuged at 2,000 g for 15 minutes at 4° C. The supernatant fractions were decanted off the pellets and washed four times with 5 volumes of water-saturated ethyl ether, and the aqueous extracts remaining were saved for assay for cyclic GMP and AMP using enzyme-immunoassay kits (Amersham Life Science Inc., Arlington Heights, IL).

Stabilities of VIPGC-NO

Figure 1:
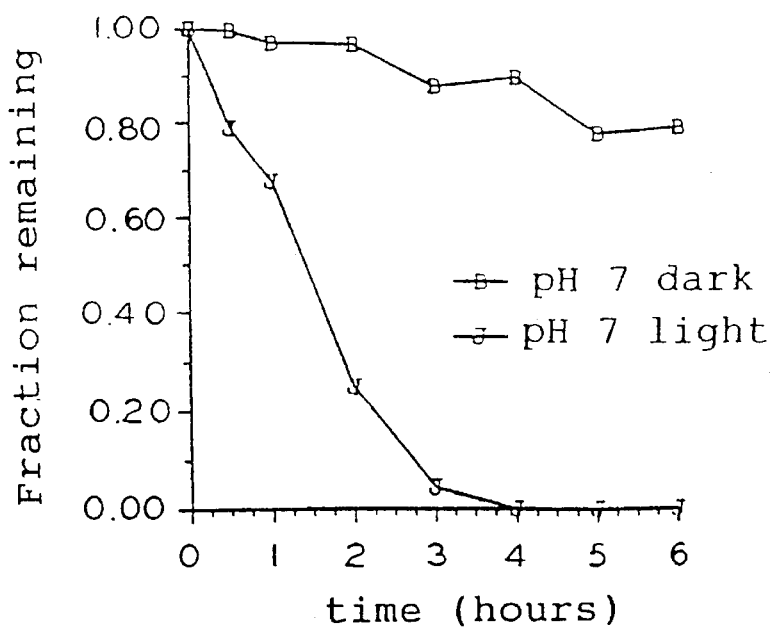
FIG. 1 illustrates the rate of photodecomposition of VIPGC-NO in the presence and absence of sunlight.

VIPGC was dissolved in 0.5N HCl, and then allowed to react with equimolar $NaNO_2$. The formation of VIPGC-NO in the mixture was either directly determined by using the colorimetric assay of Saville, or detected immediately after titrating the mixture to pH 7.0 with 1.0N NaOH. In order to study photo-effects on VIPGC-NO stabilities, samples were sealed in eppendorf test tubes and the tubes were exposed to sunlight from window for a uniform period. VIPGC-NO in the samples exposed to sunlight decayed faster than VIPGC-NO samples stored in dark regardless of what the pH values of the samples were (FIG. 1).

Effects of VIP, VIPGC, VIPGC-NO and GSNO on rabbit aortic rings

Figure 2:
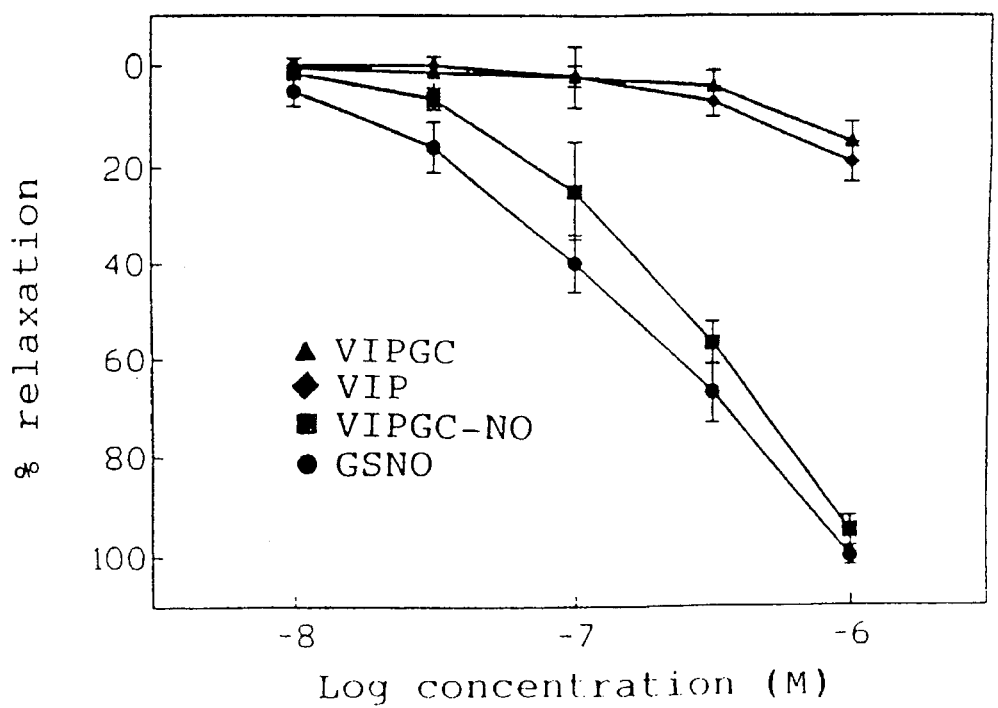
FIG. 2 shows a comparison of the effects of VIPGC-NO, VIP, VIPGC and GSNO on tension of rabbit aortic rings.

In intact aortic rings precontracted with phenylephrine (100 µM), the addition of VIPGC-NO produced relaxations in a dose-dependent manner, which was also observed in the rings exposed to GSNO in a dose range from 10 nM to 1 µM. However, in time-matched aortic rings from same rabbit, successive cumulative additions of VIP and VIPGC produced certain degree of relaxation only at 1 µM (FIG. 2).

Figure 3A:
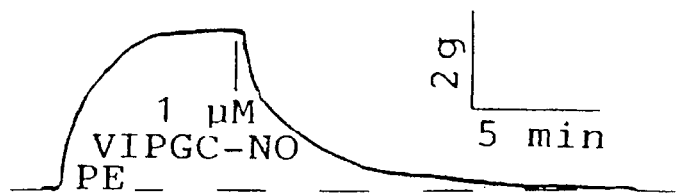
FIG. 3A shows the effects of VIPGC-NO on relaxation of rabbit aortic rings over time and FIG. 3B shows the effects of VIP under the same conditions.
Figure 3B:
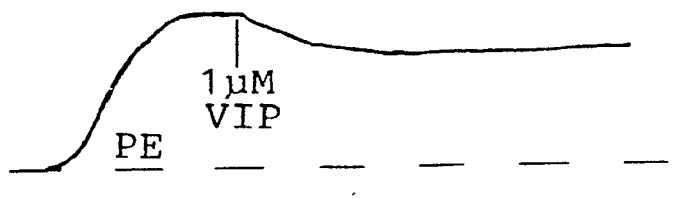

On phenylephrine-precontracted aortic rings of rabbit, single doses (1 µM) of VIPGC-NO induced complete vasorelaxations that were of rapid onset and sustained duration (FIG. 3). In comparison with VIPGC-NO, the same doses of VIP only produced 19±4% (n=3) relaxation.

Effects of VIP, VIPGC, VIPGC-NO on guinea-pig trachea

Figure 4:
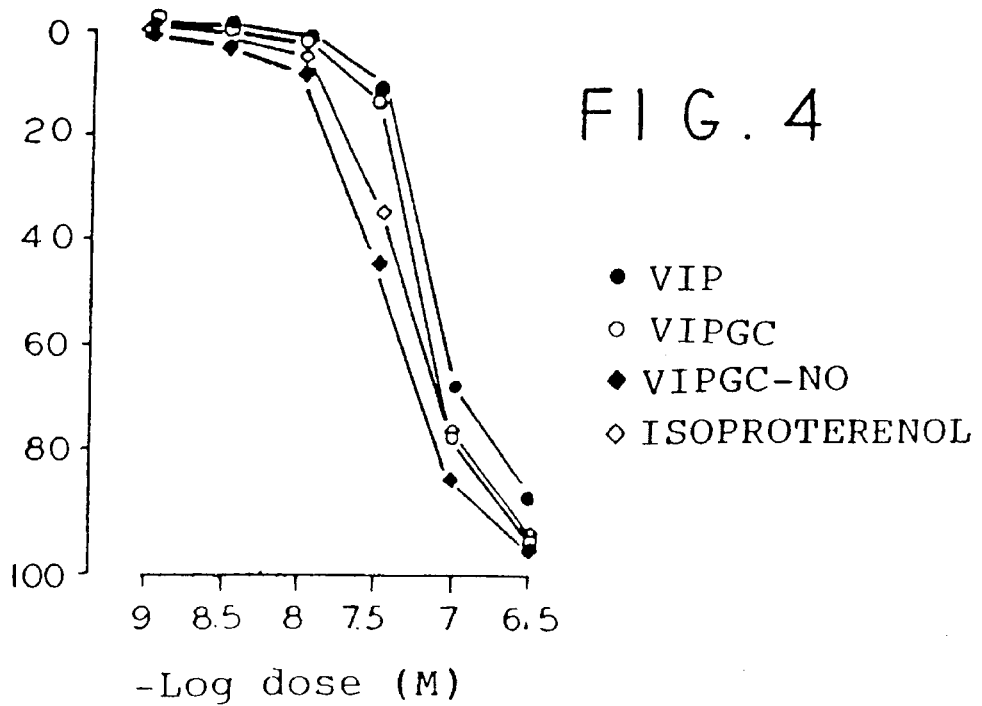
FIG. 4 shows a comparison of effects of isoproterenol, VIP, VIP-GC and VIPGC-NO on tension of tracheal rings of guinea pigs.

VIP-like immunoreactivity has been found in guinea pig airway neurons. To compare the potency of VIP and its nitrosylated analog VIPGC-NO in relaxing airway, dose-response curves for VIP, VIPGC-NO and VIPGC in the isolated guinea-pig trachea precontracted with 10 µM methacholine were first made (FIG. 4). VIP, VIPGC-NO and VIPGC produced relaxation of tracheal rings with $IC_{50}$ of 74±5 nM, 32±6 nM and 59±9 nM (all n=4), respectively. In contrast, isoproterenol caused relaxations of the tracheal rings with $IC_{50}$ 47±3 nM. The relaxations of guinea pig trachea by VIP, VIPGC-NO and VIPGC (all 100 nM) reached a plateau in about 20 minutes. In contrast, 100 nM isoproterenol reached a plateau of tracheal relaxations in about 5 minutes. Pretreatment of the tracheal rings with 100 nM propanol only blocked the airway relaxation induced by cumulative additions of the isoproterenol in a dose range 10–320 nM. However, propanol did not antagonize the relaxation induced by VIP, VIPGC, and VIPGC-NO in the same dose range.

Effects of VIP, VIPGC, VIPGC-NO and GSNO on Sphincter of Oddi

Figure 5:
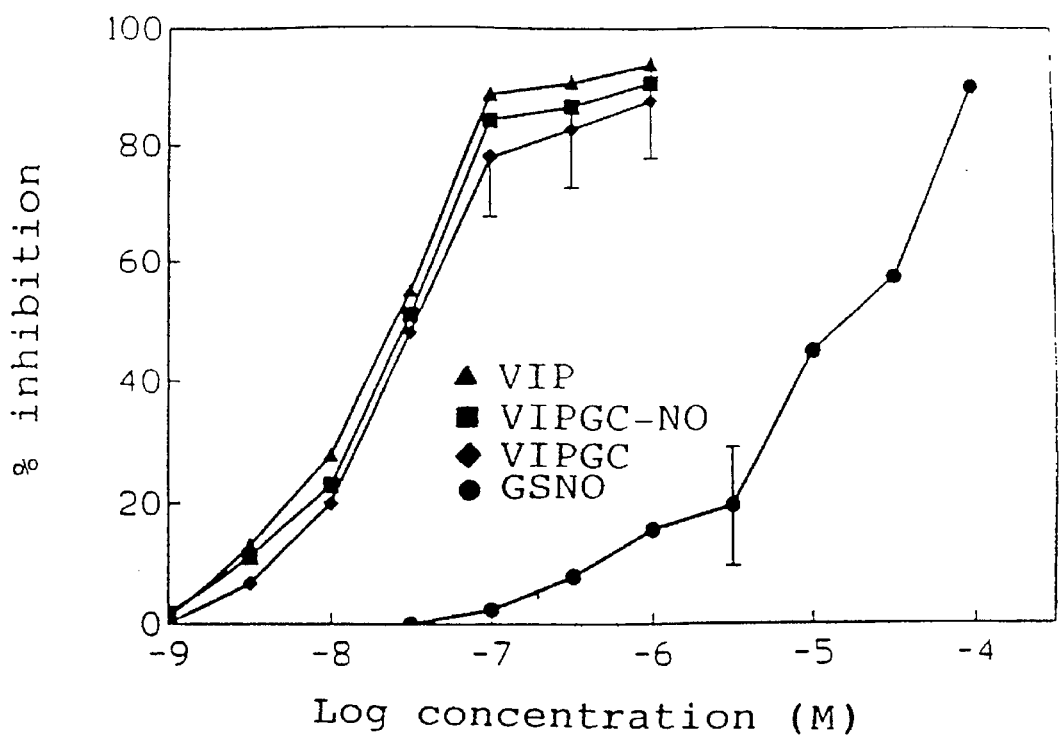
FIG. 5 shows the effects of VIPGC-NO, VIP, VIP-GC and GSNO on the contraction frequency of rabbit Sphincter of Oddi.
Figure 6:
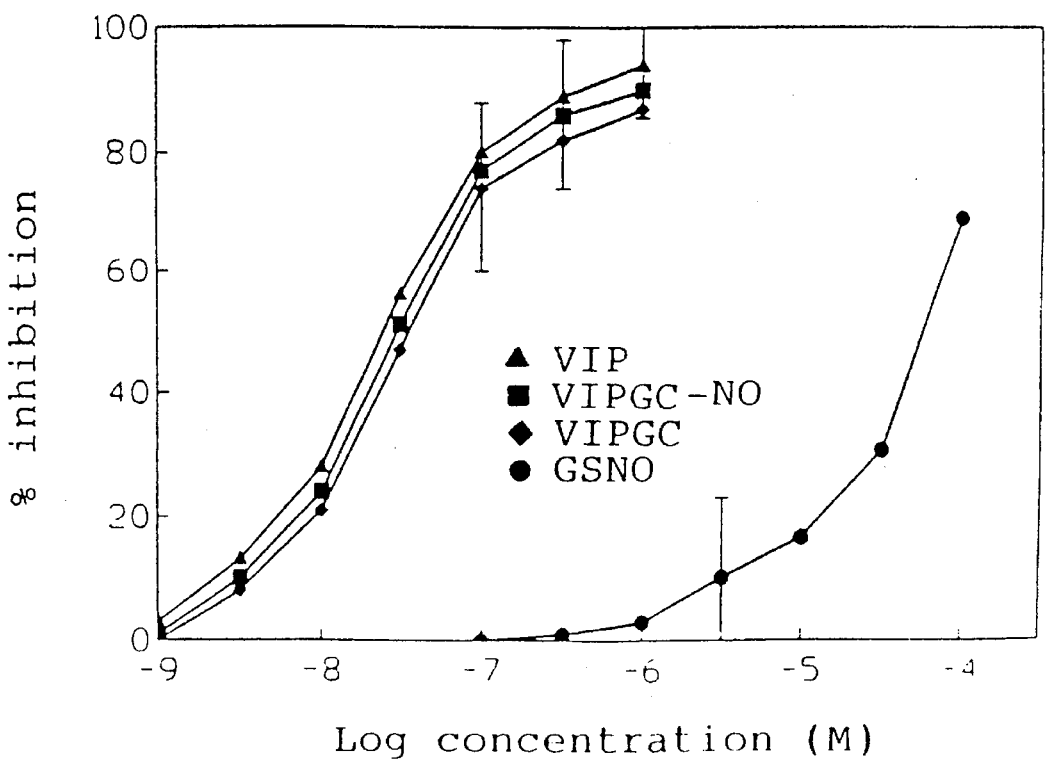
FIG. 6 shows the effects of VIPGC-NO, VIP, VIPGC and GSNO on contraction amplitude of rabbit Sphincter of Oddi.

After equilibrated in oxygenated Krebs at 37° C. for about 30 minutes, all isolated rabbit SO recover intrinsic rhythmic contractility. The average contraction frequency and amplitude were 8.0±0.6/min and 540±60 mg (mean ±S.E.M., n=20), respectively. Cumulative addition of VIP, VIPGC-NO and VIPGC in a dose range of 1 nM- 1 µM inhibited both basic contraction frequency and amplitude dose-dependently (FIG. 5, 6). Effects of these compounds were observed within 2 minutes after addition of them to the organ chambers and persisted at least 90 minutes. At 1 µM level, VIP, VIPGC-NO, and VIPGC inhibited the contraction frequency by 94±16% (n=6), 91±10% (n=7) and 88±12% (n=4), respectively, whereas GSNO was observed to be significantly less potent: at 100 µM, GSNO inhibited the basic contractility of sphincter of Oddi by 91±9% (n=3).

Addition of acetylcholine (ACh) produced a dose-dependent increase in basal pressure. Final concentration of ACh (10 µM) resulted in 69±15% acceleration in phasic contractions and 73±12% elevations in tonic pressure (n=12). On ACh-pretreated (10 µM) rabbit sphincter of Oddi, cumulative addition of VIP, VIPGC-NO, VIPGC (1 nM- 1 µM) and GSNO (0.1 µM- 100 µM) gradually attenuated the ACh-induced contractions of sphincter of Oddi. VIP, VIPGC-NO and VIPGC (1 µM) as well as GSNO (100 µM) inhibited ACh-enhanced (10 µM) phasic contractions of sphincter of Oddi by 93±7%, 90±3%, 72±22% and 89±5%, respectively.

Figure 7B:
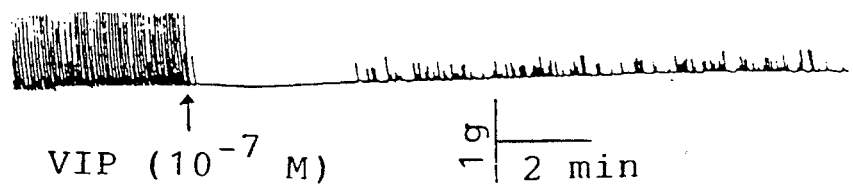

In order to compare the potency of inhibition by VIP to VIPGC-NO on phasic contraction of sphincter of Oddi, the tissues were incubated with single doses (0.1 µM) of VIP or VIPGC-NO for 30 minutes (FIG. 7). During the period of the incubation, the irregular and incomplete contractions of the sphincter of Oddi were noted more frequently (40±11 (n=5)) in the presence of 0.1 µM VIP than in the presence of 0.1 µM VIPGC-NO (26±13, n=5, P<0.05).

Effects of VIP, VIPGC, VIPGC-NO and GSNO on gastric fundus strips

Gastric fundus strips of rats, when incubated in oxygenated Krebs at 37° C., developed intrinsic rhythmic contractility within 30 minutes. The addition of 5HT (10 µM) produced significant increase in contractions of the strips. The average contraction amplitude and frequency of the strips were 1.1±0.2 g and 24±2/ 10 min (n=17). Again, VIPGC appeared less potent than VIPGC-NO; however, potentiation of native VIP's effect was not observed. Isoproterenol and GSNO were the two least potent inhibitors (FIG. 8).

Effects of VIP, VIPGC, VIPGC-NO and GSNO on the cGMP and cAMP content of aortic rings and tracheal rings Pretreatment of rabbit aortic rings with VIPGC-NO, GSNO resulted in a significant increase in cGMP concentration (both P<0.01) when these rings reached a maximum relaxation. In time-matched aortic rings from the same rabbits, incubation of aortic rings with VIP or VIPGC produced an increase in cGMP level as well; however, the increase in cGMP content induced by VIP or VIPGC was less than that of VIPGC-NO or GSNO (FIG. 9). There was no significant increase in cAMP content when simultaneous determination of cAMP with cGMP were made on the same tissue pretreated with VIP, VIPGC, VIPGC-NO or GSNO (all 1 µM; FIG. 9).

When tracheal rings of guinea pigs reached a plateau of relaxation induced by VIPGC-NO, VIP and VIPGC (all 100 nM, n=4), a significant increase in the content of cGMP was observed. However, there were no concomitant increases in the cAMP level of those tissues pretreated with VIPGC-NO and its analogs (FIG. 10). Isoproterenol (100 nM) produced significant increase in the cAMP level (P<0.05, n=4) with no appreciable changes in the cGMP content compared to the time-matched controls (FIG. 10).

EXAMPLE 3

Organ Chamber Studies of Corpus Cavernosum Reactivity

Male New Zealand White rabbits (3.0–3.5 Kg.) were sacrificed with an intravenous dose of pentobarbital (50 mg/kg) and exanguinated. Rabbit penises were surgically removed en bloc, with care being taken to keep the tunica albuginea intact. The corpus spongiosum and urethra were excised. The corpus cavernosum tissue was carefully dissected free from the surrounding tunica albuginea.

Strips of corpus cavernosum tissue measuring approximately 3 mm×3 mm×10 mm were submerged in physiological salt solution (118.3 mM NaCl; 4.7mM KCl; 0.6mM $MgSO_4$; 1.2 mM $K_2PO_4$; 2.5 mM $CaCl_2$; 25 mM $NaHCO_3$; 0.026 mM CaNa EDTA; and 11.1 mM glucose) in water jacketed organ chambers (25 ml). The strips were attached with silk ties to a wire connected to a force transducer, on one end, and fixed with silk ties to a metallic support on the opposite end. The solution was gassed with 95% air and 5% $CO_2$ which ensured a $pO_2$ in the solution of about 150 mm Hg and a pH of 7.3–7.5. The temperature was maintained at 37° C. by circulation of warm distilled water through the water jacketed chambers. The corpus cavernosum tissue was then stretched incrementally until the optimal isometric tension for contraction, for each strip, was attained. After every 3 stretches (1–1.5 grams tension/stretch), the tissue was contracted with phenylephrine (1.0 µM). Once a stable maximal contraction to phenylephrine was attained, this response was compared to the previous one. When the amplitude of the contraction was within 10% of the previous contraction, that tension was considered the optimal resting isometric tension for contraction. The optimal isometric tension for contraction for rabbit corpus cavernosum tissue was about 4 grams.

In each experiment three different strips of rabbit corpus cavernosum tissue were contracted with 5 to 7±10$^{-7}$M phenylephrine. Once a stable contraction was attained the strips were exposed to either VIP, VIP-Gly-Cys-NO, or VIP-Gly-Cys-$NH_2$. These molecules were put in solution in distilled water and added to the organ chamber in cumulative half log increments, starting at an organ chamber concentration of 10$^{-9}$M and up to a concentration of 10$^{-5}$M.

Relaxations within a dose response curve were measured from a common reference line denoting the amount of stable tone which the tissue achieved with phenylephrine before exposure to VIP or its analogs (0% relaxation). The perpendicular vertical distance between this reference line and the largest downward deflection in the tracing at any given dose was recorded as the response at that dose. All responses are expressed as percentage of maximal relaxation which was induced by the addition of 0.1 mM papaverine at the end of the experiment. Data are expressed as means ± SE for n different animals.

FIG. 11 shows a comparison of the responses of rabbit corpus cavernosum tissue to VIP-Gly-Cys-NO (SNO-VIP) and VIP-Gly-Cys-NH$_2$ (VIPGC). Rabbit corpus cavernosum strips contracted with phenylephrine (5 to 7×10$^{-7}$M) were exposed to cumulative concentrations of either VIPGCNO or VIPGC. This experiment demonstrates that the addition of Gly-Cys to VIP maintains the biological activity of the new molecule. Furthermore, at the maximal effective concentration (3×10$^{-6}$M) for both compounds tested, VIPGCNO is a more potent relaxant that VIPGC. This difference is attributable to the NO donor capability of VIPGCNO that is not present in VIPGC.

FIG. 12 shows a comparison of the responses of rabbit corpus cavernosum tissue to VIP-Gly-Cys-NO (SNO-VIP) and VIP. Rabbit corpus cavernosum strips contracted with phenylephrine (5 to 7×10$^{-7}$M) were exposed to cumulative concentrations of either vipgcno or VIP. This experiment demonstrates that at the maximal effective concentration (3×10$^6$M) for both compounds tested, VIPGCNO is a more potent relaxant than VIP.

EXAMPLE 4

In Vivo Studies in Canine Animal Model

Male mongrel dogs (20–30 kg) were used as the animal model. Under pentobarbital anesthesia (30 mg/kg) and mechanical respiration, a 20 gauge anglocatheter was placed into the carotid artery for measurement of systemic blood pressure. A ventral incision was made in the penis and the corpora cavernosa were exposed. In the dog the right and left corpora do not communicate.

A 19 gauge minicatheter was inserted deep into the cavernosal tissue, on each corpus, for pressure measurement and delivery of either VIP, VIP-Gly-Cys-NO, VIP-Gly-Cys-NH$_2$ or papaverine. Since the corpus do not communicate, whenever two analogs of VIP were compared in the same animal, one corpus was used to test one analog and the other corpus to test the other. Drugs were delivered intracavernosally in solution, 0.5 ml volume, at variable syringe concentrations, starting at 10$^{-7}$M and progressively increasing the dose up to, in some instances, 10$^{-4}$M. In most experiments, at the end, papaverine 80 mM was administered intracavernosally in order to compare this response to those elicited by VIP or its analogs. At all times systemic blood pressure was monitored, for comparison with intracavernosal pressure.

FIG. 13 shows erectile response in vivo in the anesthetized dog following the injection of 10$^{-5}$M VIP or papaverine (8×10$^{-2}$M). The ordinate is intracavernosal pressure (mm Hg) and the abscissa is time (duration of the erectile response, in 100 second increments). Diastolic blood pressure (DBP) immediately before and after the administration of papaverine or VIP were 110→55 mm Hg. This experiment shows that intracavernosal VIP is capable of inducing sustained penile erection in this model. In both cases there was a significant drop in blood pressure following intracavernosal administration of treatment.

FIG. 14 shows a comparison of the erectile response in vivo in the anesthetized dog upon intracavernosal administration of either VIPGC or SNO-VIP. The ordinate is intracavernosal pressure (mm Hg) and the abscissa is time (duration of the erectile response, in 100 second increments). Diastolic blood pressures(DBP) immediately before and after the administration of VIP-GC or SNO-VIP were as follows: 1×10$^{-4}$M VIP-GC(100 mm Hg, unstable); 1×10$^{-4}$ M SNO-VIP(100→90 mm Hg); 3×10$^{-5}$M VIP-GC(115 →100 mm Hg); 3×10$^{-5}$M SNO-VIP(115→65 mm Hg); 1×10$^{-5}$M VIP-GC (120→95 mm Hg); 1×10$^{-5}$M SNO-VIP(115→100 mm Hg); 1×10$^{-6}$M SNO-VIP(120 mm Hg); 1×10$^{-7}$M SNO-VIP(115 mm Hg). VIP-GC was injected in one corpus and SNO-VIP in the other. Doses of 3×10$^{-7}$ and 10$^{-6}$M (0.5 ml in each case) SNO-VIP caused partial erectile responses, while 3×10$^{-7}$ and 10$^{-6}$M VIPGC had no effect-(not shown). There was no response to 3×10$^6$M SNO-VIP or VIP-GC(DBP=120 mm Hg). At the maximal concentration tested (10$^{-4}$M) VIP-GC and SNO-VIP caused and increase in intracavernosal pressure of similar magnitude, but the duration of the response was longer with SNO-VIP. As shown in the notations, treatments had no effect on diastolic blood pressure at concentrations below 10$^{-5}$M. Higher concentrations did produce temporary hypotension.

FIG. 15 shows a comparison of the erectile response in vivo in the anesthetized dog upon intracavernosal administration of either VIP-GC or SNO-VIP. The ordinate is intracavernosal pressure (mm Hg) and the abscissa is time (duration of the erectile response, in 100 second increments). Diastolic blood pressures (DBP) immediately before and after the administration of VIP-GC or SNO-VIP were as follows: 1×10$^{-5}$M VIP-GC(110→40 mm Hg); 1×10$^{-5}$M SNO-VIP(110 mm Hg); 3×10$^{-6}$M VIP-GC(120→110 mm Hg); 3×10$^{-6}$M SNO-VIP(120 mm Hg); 1×10$^{-6}$M SNO-VIP(115 mm Hg). VIP-GC was injected in one corpus and SNO-VIP in the other. As shown, SNO-VIP (10$^{-6}$M) induced a partial erectile response while the same concentration of VIP-GC had no effect(not shown). At the highest concentrations tested (10$^{-5}$M) SNO-VIP and VIP-GC caused comparable erectile responses, although SNO-VIP was slightly more potent (higher intracavernosal pressure and more rapid onset).

FIG. 16 shows a comparison of the erectile response in vivo in the anesthetized dog upon administration of either VIP, SNO-VIP or papaverine. The ordinate is intracavernosal pressure (mm Hg). The abscissa is time (duration of the erectile response, in 100 second increments). Diastolic blood pressures (DBP) immediately before and after the administration of VIP, SNO-VIP or papaverine were as follows: 80 mM papaverine +SNO-VIP(100→85 mm Hg); 80 mM papaverine +VIP(100→85 mm Hg); 3×10$^{-5}$M(95→50 mm Hg); 1×10$^{-5}$M VIP(60→5 mm Hg); 1×10$^{-5}$M SNO-VIP(80 mm Hg). As shown, VIP (10-5 M) caused a partial and short erectile response while the same concentration of SNO-VIP caused a larger and more sustained erection.

What is claimed is:

1. A compound comprising a neuropeptide or analog, fragment or derivative thereof having vascular or non-vascular smooth muscle relaxant activity to which has been directly or indirectly linked at least one NO or NO$_2$ group.

2. The compound of claim 1 wherein the neuropeptide is selected from the group consisting of peptide histidine isoleucine, peptide histidine methionine, substance P, calcitonin gene-related peptide and a tachykinin.

3. The compound of claim 1 which comprises vasoactive intestinal peptide conjugated with a nitric oxide or nitric oxide-releasing moiety.

4. The compound of claim 3 which has the structure vasoactive intestinal peptide-glycine-cysteine-NO.

5. The compound of claim 1 which is a fragment of vasoactive intestinal peptide selected from the group consisting of those having peptides 1–6, 18–28, 15–28, 14–28 and 7–28 of the vasoactive intestinal peptide.

6. The compound of claim 1 which is a vasoactive intestinal peptide analog selected from the group consisting of the analog in which amino acid 11 is serine, the analog wherein amino acid 13 is phenylalanine, the analog wherein amino acid 26 is valine and the analog wherein amino acid 28 is threonine.

7. The compound of claim 1 which is a vasoactive intestinal peptide fragment having amino acids 11 to 23 thereof.

8. The compound of claim 1 which is a vasoactive intestinal peptide fragment having amino acids 15–20 thereof.

9. A composition comprising the compound of claim 1 in a pharmaceutically acceptable carrier.

10. A composition comprising the compound of claim 3 in a pharmaceutically acceptable carrier.

11. A method for relaxing vascular smooth muscle which comprises contacting said vascular smooth muscle with a vascular smooth muscle relaxing amount of the compound of claim 1.

12. A method for relaxing vascular smooth muscle which comprises contacting said vascular smooth muscle with a vascular smooth muscle relaxing amount of the compound of claim 3.

13. A method for the treatment of disease states responsive to the prevention or relaxation of undesirable contractions of vascular smooth muscle which comprises administering a vascular smooth muscle relaxing amount of the composition of claim 9 to an individual in need thereof.

14. A method for the treatment of disease states responsive to the prevention or relaxation of undesirable contractions of vascular smooth muscle which comprises administering a vascular smooth muscle relaxing amount of the composition of claim 10 to an individual in need thereof.

15. A method for preventing or treating vascular disorders involving vascular smooth muscle contraction which comprises administering to an individual in need thereof an amount of the composition of claim 9 effective to prevent or treat vascular disorders involving vascular smooth muscle contraction.

16. A method for preventing or treating vascular disorders involving vascular smooth muscle contraction which comprises administering to an individual in need thereof an amount of the composition of claim 10 effective to prevent or treat vascular disorders involving vascular smooth muscle contraction.

17. A method for relaxing non-vascular smooth muscle which comprises contacting said non-vascular smooth muscle with a non-vascular smooth muscle relaxing amount of the compound of claim 1.

18. A method for relaxing non-vascular smooth muscle which comprises contacting said non-vascular smooth muscle with a non-vascular smooth muscle relaxing amount of the compound of claim 1.

19. A method for the treatment of disease states responsive to the prevention or relaxation of undesirable contractions of non-vascular smooth muscle which comprises administering a non-vascular smooth muscle relaxing amount of the composition of claim 9 to an individual in need thereof.

20. A method for the treatment of disease states responsive to the prevention or relaxation of undesirable contractions of non-vascular smooth muscle which comprises administering a non-vascular smooth muscle relaxing amount of the composition of claim 10 to an individual in need thereof.

21. A method for relaxing airway smooth muscle which comprises contacting said airway smooth muscle with an airway smooth muscle relaxing amount of the compound of claim 1.

22. A method for relaxing airway smooth muscle which comprises contacting said airway smooth muscle with an airway smooth muscle relaxing amount of the compound of claim 3.

23. A method for the treatment of disease states responsive to the prevention or relaxation of undesirable contractions of airway smooth muscle which comprises administering an airway smooth muscle relaxing amount of the composition of claim 9 to an individual in need thereof.

24. A method for the treatment of disease states responsive to the prevention or relaxation of undesirable contractions of airway smooth muscle which comprises administering an airway smooth muscle relaxing amount of the composition of claim 10 to an individual in need thereof.

25. A method for preventing or treating an obstructive lung disorder selected from the group consisting of emphysema, asthma, bronchitis, fibrosis, excessive mucous secretion, obstruction of air flow and post-surgical complications which comprises administering to an individual in need thereof an amount effective to prevent or treat an obstructive lung disorder selected from the group consisting of emphysema, asthma, bronchitis, fibrosis, excessive mucous secretion, obstruction of air flow and post-surgical complications of the composition of claim 9.

26. A method for preventing or treating an obstructive lung disorder selected from the group consisting of emphysema, asthma, bronchitis, fibrosis, excessive mucous secretion, obstruction of air flow and post-surgical complications which comprises administering to an individual in need thereof an amount effective to prevent or treat an obstructive lung disorder selected from the group consisting of emphysema, asthma, bronchitis, fibrosis, excessive mucous secretion, obstruction of air flow and post-surgical complications of the composition of claim 10.

27. A method for relaxing gastrointestinal smooth muscle which comprises contacting said gastrointestinal smooth muscle with a gastrointestinal smooth muscle relaxing amount of the compound of claim 1.

28. A method for relaxing gastrointestinal smooth muscle which comprises contacting said gastrointestinal smooth muscle with a gastrointestinal smooth muscle relaxing amount of the compound of claim 3.

29. A method for the treatment of disease states responsive to the prevention or relaxation of undesirable contractions of gastrointestinal smooth muscle which comprises administering a gastrointestinal smooth muscle relaxing amount of the composition of claim 9 to an individual in need thereof.

30. A method for the treatment of disease states responsive to the prevention or relaxation of undesirable contractions of gastrointestinal smooth muscle which comprises administering a gastrointestinal smooth muscle relaxing amount of the composition of claim 10 to an individual in need thereof.

31. A method for preventing or treating gastrointestinal smooth muscle contractions or spasms associated with an endoscopic procedure which comprises administering to an individual in need thereof an amount effective to prevent or treat gastrointestinal smooth muscle contractions or spasms associated with an endoscopic procedure of the composition of claim 9.

32. A method for preventing or treating gastrointestinal smooth muscle contractions or spasms associated with an endoscopic procedure which comprises administering to an individual in need thereof an amount effective to prevent or treat gastrointestinal smooth muscle contractions or spasms associated with an endoscopic procedure of the composition of claim 10.

33. A method for relaxing corpus cavernosum smooth muscle which comprises contacting said corpus cavernosum smooth muscle with a corpus cavernosum smooth muscle relaxing amount of the compound of claim 1.

34. A method for relaxing corpus cavernosum smooth muscle which comprises contacting said corpus cavernosum smooth muscle with a corpus cavernosum smooth muscle relaxing amount of the compound of claim 3.

35. A method for the treatment of disease states responsive to the prevention or relaxation of undesirable contractions of corpus cavernosum smooth muscle which comprises administering a corpus cavernosum smooth muscle relaxing amount of the composition of claim 9 to an individual in need thereof.

36. A method for the treatment of disease states responsive to the prevention or relaxation of undesirable contractions of corpus cavernosum smooth muscle which comprises administering a corpus cavernosum smooth muscle relaxing amount of the composition of claim 10 to an individual in need thereof.

37. A method for preventing or treating human male impotence which comprises administering to a human male in need thereof an amount effective to prevent or treat human male impotence of the composition of claim 9.

38. A method for preventing or treating human male impotence which comprises administering to a human male in need thereof an amount effective to prevent or treat human male impotence of the composition of claim 10.

39. The method of claim 38 wherein administration is parenteral.

40. The method of claim 39 wherein administration is by injection into the corpus cavernosum, intraurethral catheterization or by topical administration.

41. The method of claim 38 wherein the vasoactive intestinal peptide is administered in a range from about 1 nM to 1 mM per kilogram of body weight.

* * * * *

UNITED STATES PATENT AND TRADEMARK OFFICE
CERTIFICATE OF CORRECTION

PATENT NO : 5,612,314
DATED : March 18, 1997
INVENTOR(S) : Stamler and de Tejada It is certified that error appears in the above-identified patent and that said Letters Patent is hereby corrected as shown below:

Line 4 of claim 18, change "1" to --3--.

Signed and Sealed this

Twenty-fifth Day of May, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO : 5,612,314
DATED : March 18, 1997
INVENTOR(S): Stamler and Saenz de Tejada It is certified that error appears in the above-identified patent and that said Letters Patent is hereby corrected as shown below:

Title page, item [75] Inventors the name of the second inventor should be changed from "Inigo S. de Tejada" to the correct name of -- Inigo Saenz de Tejada --.

Signed and Sealed this

Sixteenth Day of November, 1999

Attest:

Q. TODD DICKINSON

Attesting Officer

Acting Commissioner of Patents and Trademarks